United States Patent
Matsuno et al.

(10) Patent No.: US 8,110,403 B2
(45) Date of Patent: Feb. 7, 2012

(54) IMMUNOASSAY METHOD

(75) Inventors: Tadahiro Matsuno, Kaisei-machi (JP); Kentaro Nakamura, Asaka (JP)

(73) Assignee: Fujifilm Corporation, Tokyo (JP)

( * ) Notice: Subject to any disclaimer, the term of this patent is extended or adjusted under 35 U.S.C. 154(b) by 360 days.

(21) Appl. No.: 12/369,547

(22) Filed: Feb. 11, 2009

(65) Prior Publication Data

US 2009/0203151 A1 Aug. 13, 2009

(30) Foreign Application Priority Data

Feb. 12, 2008 (JP) .................. 2008-029982

(51) Int. Cl.
*G01N 30/02* (2006.01)
*G01N 21/75* (2006.01)
*C12M 3/00* (2006.01)

(52) U.S. Cl. ........ 436/161; 436/518; 436/523; 436/533; 436/166; 436/172; 436/177; 436/178; 435/7.1; 435/7.94; 435/287.2; 435/287.9; 435/288.6; 422/82.08; 422/82.09

(58) Field of Classification Search .................. 436/518, 436/523, 524, 528, 533, 10, 56, 161, 166, 436/172, 177, 178; 435/6, 7.1, 7.2, 7.92, 435/7.94, 287.2, 287.7, 287.9, 288.3, 288.6; 422/82.08, 82.09
See application file for complete search history.

(56) References Cited

U.S. PATENT DOCUMENTS 6,630,307 B2 * 10/2003 Bruchez et al. .................. 435/6
7,413,868 B2 * 8/2008 Kauvar et al. .................. 435/7.2

FOREIGN PATENT DOCUMENTS

| JP | 3-167475 A | 7/1991 |
| JP | 3-216553 A | 9/1991 |
| JP | 8-5635 A | 1/1996 |
| JP | 8005635 * | 1/1996 |

(Continued)

OTHER PUBLICATIONS

Office Action dated Aug. 16, 2011 issued in corresponding Japanese Patent Application No. 2008-029982.

*Primary Examiner* — Gail R Gabel
(74) *Attorney, Agent, or Firm* — Birch, Stewart, Kolasch & Birch, LLP

(57) ABSTRACT

It is an object of the present invention to provide an immunoassay method which is capable of simultaneous quantification of a plurality of test substances under a same analysis condition, through adjustment of the measurement sensitivity/range by simply varying the size of particles for use as labels, without changing the spectra of these particles. The present invention provides an immunoassay method which comprises: simultaneously or step-by step developing respective of the plurality of the test substances and respective of labeling substance particles labeled with first binding substance against the respective of the plurality of the test substances on an insoluble carrier; capturing the test substances and the labeling substance particles in reaction portions on the insoluble carrier that has been immobilized with the respective of second binding substances against the respective of the plurality of the test substances at different positions; and measuring optical characteristic of the labeling substance particles, so as to simultaneously detect the plurality of the test substances, wherein the plurality of the test substances having different detection concentration ranges are simultaneously detected with use of the labeling substance particles which are different in the particle size corresponding to the test substances.

7 Claims, 1 Drawing Sheet

FOREIGN PATENT DOCUMENTS

| | | | |
|---|---|---|---|
| JP | 10-132817 | A | 5/1998 |
| JP | 10132817 | * | 5/1998 |
| JP | 2002-544488 | A | 12/2002 |
| JP | 2005-510706 | A | 4/2005 |
| JP | 2006-38700 | A | 2/2006 |
| JP | 2007-510929 | A | 4/2007 |
| JP | 2007-537428 | A | 12/2007 |
| WO | WO 00/68692 | A1 | 11/2000 |
| WO | WO 03/029822 | A1 | 4/2003 |
| WO | WO 2005/045396 | A2 | 5/2005 |
| WO | WO 2005/045396 | A3 | 5/2005 |

* cited by examiner

IMMUNOASSAY METHOD

TECHNICAL FIELD

The present invention relates to an immunoassay method for simultaneously detecting or quantifying a plurality of test substances having different detection concentration ranges.

BACKGROUND ART

In conventional immunoassays using antibodies, an antibody against a test substance is labeled with fine particle(s) of a fluorescent dye, an enzyme, a gold colloid or the like, and then the labeling substance is detected. Among them, when a plurality of test substances are to be simultaneously detected on a same support, there have been known methods in which the color tones of particles for labeling respective antibodies are varied so as to thereby carry out visual determination (JP Patent Publication (Kokai) No. 8-5635 A (1996) and JP Patent Publication (Kokai) No. 10-132817 A (1998)). However, although these methods are deemed to be excellent methods in terms of visual detection of test substances, they are disadvantageous when it comes to quantitative analysis of the test substances, because a plurality of detection systems have to be prepared corresponding to the light absorption wavelengths of the labels, which makes the detector complicated and expensive.

In addition, when analysis targets having different ranges of required measurement concentration are to be quantified with a same detector, general methods are such that a low-sensitive detection system is selected for a test substance at high concentration, as well as previously diluting a sample containing the test substance either by means of manual technique or an analyzer. Therefore, it has been difficult to quantify test substances having different ranges of required measurement concentration, on a same carrier.

DISCLOSURE OF THE INVENTION

Conventionally, when analysis targets in different ranges of required measurement concentration are to be quantified with a same detector, there have been disadvantages such that dilution/dispensation operations by means of manual technique or an analyzer are required, which makes the operations complicated and makes the analyzer large-scaled and expensive. It is an object of the present invention to provide an immunoassay method which is capable of simultaneous quantification of a plurality of test substances under a same analysis condition, through adjustment of the measurement sensitivity/range by simply varying the size of particles for use as labels, without changing the spectra of these particles.

In view of the above problems, the inventors of the present invention have conducted intensive studies. As a result, they have found that, in a method for quantifying a plurality of test substances having different ranges of required measurement concentration, on a same carrier, it is possible to simultaneously quantify such a plurality of test substances under a same analysis condition with a same apparatus, through adjustment of the measurement sensitivity/range by simply varying the size of particles for use as labels, without changing the spectra of these particles. This has led to the completion of the present invention.

The present invention provides an immunoassay method which comprises: simultaneously or step-by step developing respective of the plurality of the test substances and respective of labeling substance particles labeled with first binding substance against the respective of the plurality of the test substances on an insoluble carrier; capturing the test substances and the labeling substance particles in reaction portions on the insoluble carrier that has been immobilized with the respective of second binding substances against the respective of the plurality of the test substances at different positions; and measuring optical characteristic of the labeling substance particles, so as to simultaneously detect the plurality of the test substances, wherein the plurality of the test substances having different detection concentration ranges are simultaneously detected with use of the labeling substance particles which are different in the particle size corresponding to the test substances.

Preferably, the respective of the plurality of the test substances and the respective of the labeling substance particles labeled with the first binding substance against the respective of the plurality of the test substances are developed on the insoluble carrier, in a state where complexes thereof are being formed.

Preferably, a sample containing the respective of the plurality of the test substances is developed on an insoluble carrier, and further then the respective of the labeling substance particles labeled with the first binding substance against the respective of the plurality of the test substances are developed on the insoluble carrier.

Preferably, the optical characteristic is absorbance, scattered light intensity, or fluorescence intensity.

Preferably, the particle is a fluorescent particle, a colored particle, or a noble metal particle.

Preferably, the binding substance is an antibody.

According to the present invention, in an immunoassay method with use of particle labels, it is possible to adjust the minimum detection sensitivity and measurement range by selecting the size of the particles, and it is possible to simultaneously detect a plurality of test substances having different ranges of required measurement concentration, on a same carrier.

BEST MODE FOR CARRYING OUT THE INVENTION

1. Immunoassay

Figure 1:
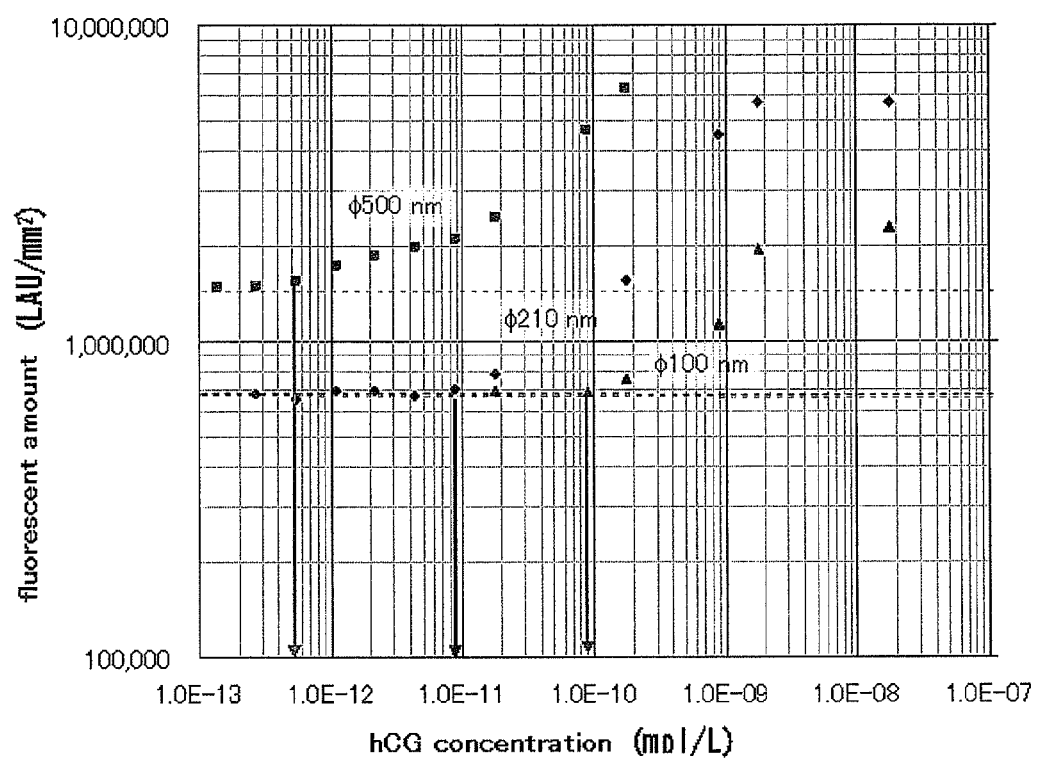
FIG. 1 shows the relationship between the particle size of antibody-labeled fluorescent particles and the detection sensitivity/range.

The immunoassay method of the present invention can be carried out by, for example, immunochromatography. In general, immunochromatography is a method for determining and/or measuring an analyte, simply, rapidly and specifically, by the following means. That is to say, a chromatographic carrier having at least one reaction zone comprising an immobilizing reagent (an antibody, an antigen, etc.) capable of binding to an analyte is used as an immobilization phase. On this chromatographic carrier, a dispersed liquid formed by dispersion of a labeling substance used in detection, which is modified by a reagent capable of binding to an analytical target, is used as a mobile phase, and the mobile phase is moved in the chromatographic carrier in a chromatographic manner. At the same time, the aforementioned analytical target specifically binds to the labeling substance used in detection, and they reach the aforementioned reaction zone. At the aforementioned reaction zone, a complex of the aforementioned analytical target and the aforementioned labeling substance used in detection specifically binds to the aforementioned immobilizing reagent. Utilizing the phenomenon whereby the labeling substance used in detection is concentrated in the immobilizing reagent portion only when the analytical target exists in an analyzed solution, the presence of a product to be detected in the analyzed solution is qualitatively and quantitatively analyzed by visual observation or using an adequate apparatus.

2. Test Sample

The type of a test sample that can be analyzed by the immunoassay method of the present invention is not particularly limited, as long as it may comprise several types of an analytical target. Examples of such a test sample include biological samples such as the body fluids of animals (particularly, a human) (e.g. blood, serum, plasma, spinal fluid, lacrimal fluid, sweat, urine, pus, runny nose, and sputum), excrements (e.g. feces), organs, tissues, mucous membranes, skin, a swab and a rinsed solution that are considered to contain them, and animals or plants themselves or the dried products thereof.

3. Pre-treatment of Test Sample

In the immunoassay method of the present invention, the aforementioned test sample can directly be used. Otherwise, the aforementioned test sample can also be used in the form of an extract obtained by extracting it with a suitable extraction solvent, or in the form of a diluted solution obtained by diluting the aforementioned extract using a suitable diluent, or in the form of a concentrate obtained by concentrating the aforementioned extract by a suitable method. As the aforementioned extraction solvent, solvents used in common immunological analysis methods (e.g. water, a normal saline solution, a buffer, etc.) or water-miscible organic solvents that enable a direct antigen-antibody reaction as a result of dilution with the aforementioned solvents can be used.

4. Structure

The type of an immunochromatographic strip that can be used in the immunoassay method of the present invention is not particularly limited, as long as it is an immunochromatographic strip that can be used in a common immunochromatography. Example of an immunochromatographic strip which can be used may include an immunochromatographic strip wherein a sample-adding pad, a labeling substance-retaining pad, a chromatographic carrier (e.g. an antibody-immobilized membrane), and an absorbent pad are disposed in this order on an adhesive sheet from the upstream to the downstream of a development direction.

4.1 Labeling Substance Particle for Detection

In the present invention, labeling substance particles labeled with first antibody against the respective of the plurality of the test substances are used. The labeling substance particle for detection is not particularly limited, so long as said labeling substance particle can be detected by measuring optical characteristic (for example, absorbance, scattered light intensity, or fluorescence intensity). Preferably, a fluorescent particle, a colored particle, or a noble metal particle can be used. As the colored particle, for example, metals such as a metal colloid can be used. The mean particle diameter of a carrier particle (or colloid) is preferably between 0.02 and 10 μm. Liposomes or microcapsules containing pigments can also be used as such colored particles. Conventionally known colored metal colloids can all be used as such colored particles for labeling. Examples of such colored metal colloids include a gold colloid, a silver colloid, a platinum colloid, an iron colloid, an aluminum hydroxide colloid, and a complex colloid thereof. Preferred examples include a gold colloid, a silver colloid, a platinum colloid, and a complex colloid thereof. A gold colloid and a silver colloid are particularly preferable in that the gold colloid exhibits a red color and the silver colloid exhibits a yellow color when they have an appropriate particle diameter. The mean particle diameter of a metal colloid is preferably between approximately 1 nm and 500 nm, more preferably between 1 nm and 100 nm. Such a metal colloid can be bound to a specifically binding substance according to conventionally known methods (e.g. The Journal of Histochemistry and Cytochemistry, Vol. 30, No. 7, pp. 691-696 (1982)). That is to say, a metal colloid is mixed with a specifically binding substance (e.g. an antibody) in a suitable buffer at room temperature for 5 or more minutes. After completion of the reaction, a precipitate obtained by centrifugation is dispersed in a solution containing a dispersant such as polyethylene glycol to obtain a metal colloid-labeled specifically binding substance of interest. When gold colloid particles are used as the metal colloid, commercially available gold colloid particles may be used. Alternatively, such gold colloid particles may be prepared by a common method, for example, by a method of reducing chlorauric acid with sodium citrate (Nature Phys. Sci., vol. 241, 20 (1973), etc.).

As the fluorescent particle, for example, a particle containing a fluorescent dye can be used. The material of the particle may include an organic substance such as polystyrene or PMMA, or an inorganic substance such as $SiO_2$. The mean particle diameter of a fluorescent particle is preferably between approximately 1 nm and 3 μm, more preferably between 10 nm and 1 μm. The fluorescent particle can be bound to a specifically binding substance according to a chemical bonding method or a physical adsorption method which are known in the art.

In the immunoassay method of the present invention, a metal colloid labeling substance or a metallic sulfide labeling substance may be used as a labeling substance for labeling an antibody or antigen which specifically binds to an analytical target (an antigen or an antibody), or for labeling a standard compound. The type of such a metal colloid labeling substance or a metallic sulfide labeling substance is not particularly limited, as long as it can be used in an ordinary immunochromatography. Examples of such a metal colloid labeling substance include a platinum colloid, a gold colloid, a palladium colloid, a silver colloid, and a mixture thereof. Examples of such a metallic sulfide labeling substance include sulfides of iron, silver, palladium, lead, copper, cadmium, bismuth, antimony, tin, and mercury. In the immunoassay method of the present invention, one or more selected from these metal colloid labeling substances and/or metallic sulfide labeling substances may be used as a labeling substance(s), and a fluorescent particle can also be used as label.

The present invention is characterized in that the labeling substance particles which are different in the particle size corresponding to the test substances are used. The particle size is not particularly limited. Generally, several types of labeling substance particles, each of which has a particle size of 10 nm to 10 μm, can be used.

4-2. Binding Substance

In the present invention, a labeling substance is labeled with a first binding substance reacting with the analyte. A first binding substance reacting with the analyte is immobilized on a labeling substance. The type of the first binding substance reacting with the analyte may be any substance so long as it has an affinity against the analyte. Examples of the first binding substance may include an antibody against the analyte (antigen), an antigen against the analyte (antibody), or an aptamer against the analyte (protein, low molecular weight compound, or the like), but are not limited thereto.

In the present invention, the insoluble carrier has (a) a second binding substance reacting with the analyte, or (b) a substance binding with the first binding substance. The type of the second binding substance reacting with the analyte may be any substance so long as it has an affinity against the analyte. Examples of the second binding substance may include an antibody against the analyte (antigen), an antigen against the analyte (antibody), or an aptamer against the analyte (protein, low molecular weight compound, or the like), but are not limited thereto. The second binding substance may be the same as or different from the first binding substance.

Examples of the substance binding with the first binding substance may be the analyte, or a substance having a zone which is recognized by the first binding substance, and may be a substance which is obtained by binding a derivative of the analyte with a protein (for example, BSA).

Preferably, the first binding substance is an antibody, and/or the second binding substance is an antibody.

In the immunochromatography of the present invention, the type of an antibody having specificity for an analytical target is not particularly limited. Examples of an antibody used herein include an antiserum prepared from the serum of an animal immunized with the analytical target, an immunoglobulin fraction purified from the antiserum, a monoclonal antibody obtained by cell fusion using the splenic cells of the animal immunized with the analytical target, and the fragments thereof (for example, F(ab')2, Fab, Fab' or Fv). Such an antibody may be prepared by a common method.

The fragmented antibody can be used regardless of animal species, subclasses, and the like. Examples of antibodies that can be used in the present invention include mouse IgG, mouse IgM, rat IgG, rat IgM, rabbit IgG, rabbit IgM, goat IgG, goat IgM, sheep IgG, and sheep IgM. They can be used as either polyclonal or monoclonal antibodies.

The fragmented antibody is a molecule having at least one antigen-binding site, which is derived from complete type-antibody, such as Fab and F(ab')2. The fragmented antibody can be obtained by enzyme or chemical treatment or using genetic engineering techniques.

4-3. Chromatographic Carrier

The chromatographic carrier is preferably a porous carrier. It is particularly preferably a nitrocellulose membrane, a cellulose membrane, an acetyl cellulose membrane, a polysulfone membrane, a polyether sulfone membrane, a nylon membrane, glass fibers, a nonwoven fabric, a cloth, threads or the like.

Usually, a substance used in detection is immobilized on a part of the chromatographic carrier to form a detection zone. The substance used in detection may be directly immobilized on a part of the chromatographic carrier via a physical or chemical bond. Alternatively, the substance used in detection may be bound physically or chemically to fine particles such as latex particles, and thereafter, the fine particles are immobilized on a part of the chromatographic carrier by trapping them thereon. After immobilization of the substance used in detection on the chromatographic carrier, the chromatographic carrier may preferably be subjected to a treatment for preventing unspecific adsorption, such as a treatment using an inert protein, and it may be then used.

4-4. Sample-adding Pad

Examples of a material for the sample-adding pad include, but are not limited to, those having uniform characteristics, such as a cellulose filter paper, glass fibers, polyurethane, polyacetate, cellulose acetate, nylon, and a cotton cloth. A sample-adding portion not only acts to receive a sample containing the added analytical target, but also acts to filter off insoluble particles, etc. contained in the sample. Moreover, in order to prevent a decrease in analysis precision occurring during the analysis due to unspecific adsorption of the analytical target contained in the sample on the material of the sample-adding portion, the material constituting the sample-adding portion may be subjected to a treatment for preventing unspecific adsorption before use.

4-5. Labeling Substance-retaining Pad

Examples of a material for the labeling substance-retaining pad include a cellulose filter paper, glass fibers, and a nonwoven fabric. Such a labeling substance-retaining pad is prepared by impregnating the pad with a predetermined amount of the labeling substance used in detection as prepared above and then drying it.

4-6. Absorbent Pad

The absorbent pad is a portion for physically absorbing the added sample as a result of the chromatographic migration and for absorbing and removing an unreacted labeling substance, etc. that is not immobilized on the detection portion of the chromatographic carrier. Examples of a material for the absorbent pad include water-absorbing materials such as a cellulose filter paper, a nonwoven fabric, a cloth or cellulose acetate. The chromatographic speed after the chromatographic leading end of the added sample has reached the absorbing portion varies depending on the material and size of the absorbent material, etc. Thus, a speed adequate for the measurement of the analytical target can be determined by selection of the material and size of the absorbent material.

5. Immunological Test Method

Hereinafter, a sandwich method which is a specific embodiment of the immunoassay method of the present invention, will be described. In the sandwich method, an analytical target can be analyzed by the following procedures, for example, but the procedures are not particularly limited thereto. First, a primary antibody and a secondary antibody having specificity for an analytical target (an antigen) have previously been prepared by the aforementioned method. In addition, the primary antibody has previously been labeled. The second antibody is immobilized on a suitable insoluble support (e.g. thin film support such as a nitrocellulose membrane, a glass fiber membrane, a nylon membrane or a cellulose membrane; or a substrate such as polystyrene, PMMA or glass), and it is then allowed to come into contact with a test sample (or an extract thereof) that is likely to contain the analytical target (the antigen). If the analytical target actually exists in the test sample, an antigen-antibody reaction occurs. This antigen-antibody reaction can be carried out in the same manner as that of an ordinary antigen-antibody reaction. At the same time of the antigen-antibody reaction or after completion of the reaction, an excessive amount of the labeled primary antibody is further allowed to come into contact with the resultant. If the analytical target exists in the test sample, an immune complex of the immobilized second antibody, the analytical target (antigen) and the labeled primary antibody is formed.

In the sandwich method, after completion of the reaction of the immobilized primary antibody, the analytical target (antigen) and the secondary antibody, the labeled secondary antibody that has not formed the aforementioned immune complex is removed. Subsequently, an optical property of a region of the insoluble support, on which the second antibody has been immobilized, is measured, so that a plurality of test substances can be simultaneously detected.

The present invention will be more specifically described in the following examples. However, these examples are not intended to limit the scope of the present invention.

EXAMPLES

Example 1

Production of Fluorescent Particles (Diameter of 100 nm) Labeled With Anti-hCG Antibodies In 250 µL of 2% fluorescent particle solution (F8801, diameter of 100 nm, Molecular Probes) were added 150 µL of 50 mM MES buffer (pH 6.0) and 100 μL of 5.0 mg/mL anti-hCG monoclonal antibody solution (Anti-hCG 5008 SP-5, Medix Biochemica), followed by stirring at room temperature for 15 minutes. 5 μL of 400 mg/mL WSC aqueous solution (Product No. 01-62-0011, Wako Pure Chemical Industries) was added thereto, followed by stirring at room temperature overnight. 50 μL of 2 mol/L glycine aqueous solution was added thereto, followed by stirring for 30 minutes. The mixture was then centrifuged (at 15,000 rpm at 4° C. for 30 minutes) to effect precipitation of particles. The supernatant was removed. The remaining matter was added with 500 μL of PBS (pH 7.4), followed by re-dispersion of the fluorescent particles with an ultrasonic washer. The mixture was further centrifuged (at 15,000 rpm at 4° C. for 30 minutes), and the supernatant was removed. Then, the remaining matter was added with 500 μL of 1% BSA-containing PBS solution (pH 7.4), followed by re-dispersion of the fluorescent particles to thereby yield an antibody-labeled fluorescent particle solution.

Example 2

Production of Fluorescent Particles (Diameter of 210 nm) Labeled With Anti-hCG Antibodies In 250 μL of 2% fluorescent particle solution (F8810, diameter of 210 nm, Molecular Probes) were added 150 μL of 50 mM MES buffer (pH 6.0) and 100 μL of 5.0 mg/mL anti-hCG monoclonal antibody solution (Anti-hCG 5008 SP-5, Medix Biochemica), followed by stirring at room temperature for 15 minutes. 5 μL of 400 mg/mL WSC aqueous solution (Product No. 01-62-0011, Wako Pure Chemical Industries) was added thereto, followed by stirring at room temperature overnight. 50 μL of 2 mol/L glycine aqueous solution was added thereto, followed by stirring for 30 minutes. The mixture was then centrifuged (at 15,000 rpm, at 4° C., for 15 minutes) to effect precipitation of particles. The supernatant was removed. The remaining matter was added with 500 μL of PBS (pH 7.4), followed by re-dispersion of the fluorescent particles with an ultrasonic washer. The mixture was further centrifuged (at 15,000 rpm at 4° C. for 15 minutes), and the supernatant was removed. Then, the remaining matter was added with 500 μL of 1% BSA-containing PBS solution (pH 7.4), followed by re-dispersion of the fluorescent particles to thereby yield an antibody-labeled fluorescent particle solution.

Example 3

Production of Fluorescent Particles (Diameter of 500 nm) Labeled With Anti-hCG Antibodies In 250 μL of 2% fluorescent particle solution (F8812, diameter of 500 nm, Molecular Probes) were added 150 μL of 50 mM MES buffer (pH 6.0) and 100 μL of 5.0 mg/mL anti-hCG monoclonal antibody solution (Anti-hCG 5008 SP-5, Medix Biochemica), followed by stirring at room temperature for 15 minutes. 5 μL of 400 mg/mL WSC aqueous solution (Product No. 01-62-0011, Wako Pure Chemical Industries) was added thereto, followed by stirring at room temperature overnight. 50 μL of 2 mol/L glycine aqueous solution was added thereto, followed by stirring for 30 minutes. The mixture was then centrifuged (at 15,000 rpm at 4° C. for 10 minutes) to effect precipitation of particles. The supernatant was removed. The remaining matter was added with 500 μL of PBS (pH 7.4), followed by re-dispersion of the fluorescent particles with an ultrasonic washer. The mixture was further centrifuged (at 15,000 rpm at 4° C. for 10 minutes), and the supernatant was removed. Then, the remaining matter was added with 500 μL of 1% BSA-containing PBS solution (pH 7.4), followed by re-dispersion of the fluorescent particles to thereby yield an antibody-labeled fluorescent particle solution.

Example 4

Preparation of Antibody-Immobilized Membrane

An antibody-immobilized membrane was prepared by immobilizing an antibody onto a nitrocellulose membrane (HiFlow Plus HF240 with a plastic lining, Millipore) cut in the size of 25 mm×200 mm, in the following manner. The membrane was oriented with one of its long sides facing downwards, and was coated, at a position of 8 mm from the bottom, with a solution of anti-hCG monoclonal antibody for immobilization (Anti-Alpha subunit 6601 SPR-5, Medix Biochemica) prepared at a concentration of 0.5 mg/mL, in a line shape having a width of about 1 mm, with use of an inkjet type applicator (BioDot). In a similar manner, the membrane was also coated, at a position of 12 mm from the bottom, with a control solution of anti-mouse IgG antibody (anti-mouse IgG (H+L), rabbit F(ab')2, Product No. 566-70621, Wako Pure Chemical Industries) prepared at a concentration of 0.5 mg/mL, in a line-shape. The coated membrane was dried at 50° C. for 30 minutes with a hot-air dryer. The membrane was immersed in 500 mL of a blocking solution (50 mM borate buffer (pH 8.5) containing 0.5 weight % casein (milk-derived, Product No. 030-01505, Wako Pure Chemical Industries)) in a vat, which was then left standing for 30 minutes. Thereafter, the membrane was transferred and immersed into 500 mL of a washing/stabilizing solution (50 mM Tris-HCl (pH 7.5) containing 0.5 weight % sucrose and 0.05 weight % sodium cholate) in a similar vat, which was then left standing for 30 minutes. The membrane was taken out from the solution, and dried at room temperature overnight to yield an antibody-immobilized membrane.

Example 5

Preparation of Immunochromatographic Membrane and Kit

The antibody-immobilized membrane prepared in Example 4 was adhered to a back pressure-sensitive adhesive sheet (ARcare 9020, NIPPN TechnoCluster). At this time, the membrane was oriented so that the long side with the line of anti-hCG antibody, among two long sides of the membrane, faced downwards. The bottom side of the antibody-immobilized membrane was adhered with a reaction solution holding pad to be overlapped by about 2 mm. Then, the bottom side of the reaction solution holding pad was adhered with a sample addition pad (glass fiber pad (Glass Fiber Conjugate Pad, Millipore) cut in the size of 18 mm×150 mm) to be overlapped by about 4 mm. Further, the top side of the antibody-immobilized membrane was adhered with a lamination of four sheets of absorbent pads (cellulose membranes cut in the size of 20 mm×150 mm each (Cellulose Fiber Sample Pad, Millipore)) to be overlapped by about 5 mm. Thus adhered member was cut with a guillotine cutter (CM4000, NIPPN TechnoCluster) in parallel to the short side of the member so that the long side of the member was cut at 5 mm intervals, to thereby prepare immunochromatographic strips of 5 mm×55 mm. Thus adhered member was cut with a guillotine cutter (CM4000, NIPPN TechnoCluster) in parallel to the short side of the member so that the long side of the member was cut at 5 mm intervals, to thereby prepare immunochromatographic strips of 5 mm×55 mm. These strips were placed in a plastic case (NIPPN TechnoCluster) for use as a testing immunochromatographic kit.

Example 6 hCG Assay Using Fluorescent Particles (Diameter of 100 nm) Labeled With Anti-hCG Antibodies A series of diluted solutions of hCG (Recombinant hCG R-506, Rohto Pharmaceutical) was prepared with 1% BSA-containing PBS (pH 7.4), and it is referred to as reaction solution A. Moreover, a solution of anti-hCG antibody-labeled fluorescent particles (diameter of 100 nm), which had been produced in Example 1, was prepared at 0.01% with 1% BSA-containing PBS (pH 7.4), and it is referred to as a reaction solution B.

The reaction solution A (50 μL) and the reaction solution B (50 μL) were mixed and left still for 1 minute, the total amount of which was then dropped on the immunochromatographic kit produced in Example 5, followed by development of the solution. 15 minutes after the development, the fluorescence intensity on the test line was measured with an image analyzer (LAS-4000, FUJIFILM). The relationship between the hCG concentration and the fluorescence intensity was plotted (FIG. 1 and Table 1).

Example 7 hCG Assay Using Fluorescent Particles (Diameter of 210 nm) Labeled With Anti-hCG Antibodies The relationship between the hCG concentration and the fluorescence intensity was plotted (FIG. 1 and Table 1) according to the method of Example 6, except for that the anti-hCG antibody-labeled fluorescent particles (diameter of 210 nm) produced in Example 2 were used for the reaction solution B.

Examples 8 hCG Assay Using Fluorescent Particles (Diameter of 500 nm) Labeled With Anti-hCG Antibodies The relation between the hCG concentration and the fluorescence intensity was plotted (FIG. 1 and Table 1) according to the method of Example 6, except for that the anti-hCG antibody-labeled fluorescent particles (diameter of 500 nm) produced in Example 3 were used for the reaction solution B.

TABLE 1

| | | Antigen concentration (M) | | | | |
|---|---|---|---|---|---|---|
| | | 1.00E−12 | 1.00E−11 | 1.00E−10 | 1.00E−09 | 1.00E−08 |
| Average particle size | 100 nm | X | X | ○ | ○ | ○ |
| | 210 nm | X | ○ | ○ | ○ | — |
| | 500 nm | ○ | ○ | ○ | — | — |

○: Detectable
X: Undetectable

Example 9

Production of Fluorescent Particles (Diameter of 100 nm) Labeled With Anti-myoglobin Antibodies In 250 μL of 2% fluorescent particle solution (F8801, diameter of 100 nm, Molecular Probes) were added 150 μL of 50 mM MES buffer (pH 6.0) and 100 μL of 5.0 mg/mL anti-myoglobin monoclonal antibody solution (Anti-hMyoglobin 7001 SPR-1, Medix Biochemica), followed by stirring at room temperature for 15 minutes. 5 μL of 400 mg/mL WSC aqueous solution (Product No. 01-62-0011, Wako Pure Chemical Industries) was added thereto, followed by stirring at room temperature overnight. 50 μL of 2 mol/L glycine aqueous solution was added thereto, followed by stirring for 30 minutes. The mixture was then centrifuged (at 15,000 rpm at 4° C. for 30 minutes) to effect precipitation of particles. The supernatant was removed. The remaining matter was added with 500 μL of PBS (pH 7.4), followed by re-dispersion of the fluorescent particles with an ultrasonic washer. The mixture was further centrifuged (at 15,000 rpm at 4° C. for 30 minutes), and the supernatant was removed. Then, the remaining matter was added with 500 μL of 1% BSA-containing PBS solution (pH 7.4), followed by re-dispersion of the fluorescent particles to thereby yield an antibody-labeled fluorescent particle solution.

Example 10

Production of Fluorescent Particles (Diameter of 500 nm) Labeled With Anti-cardiac Troponin I Antibodies In 250 μL of 2% fluorescent particle solution (F8812, diameter of 500 nm, Molecular Probes) were added 150 μL of 50 mM MES buffer (pH 6.0) and 100 μL of 5.0 mg/mL anti-cardiac troponin I monoclonal antibody solution (Anti-hcTNI 9701 SPRN-5, Medix Biochemica), followed by stirring at room temperature for 15 minutes. 5 μL of 400 mg/mL WSC aqueous solution (Product No. 01-62-0011, Wako Pure Chemical Industries) was added thereto, followed by stirring at room temperature overnight. 50 μL of 2 mol/L glycine aqueous solution was added thereto, followed by stirring for 30 minutes. The mixture was then centrifuged (at 15,000 rpm at 4° C. for 30 minutes) to effect precipitation of particles. The supernatant was removed. The remaining matter was added with 500 μL of PBS (pH 7.4), followed by re-dispersion of the fluorescent particles with an ultrasonic washer. The mixture was further centrifuged (at 15,000 rpm at 4° C. for 30 minutes), and the supernatant was removed. Then, the remaining matter was added with 500 μL of 1% BSA-containing PBS solution (pH 7.4), followed by re-dispersion of the fluorescent particles to thereby yield an antibody-labeled fluorescent particle solution.

Example 11

Preparation of Antibody-Immobilized Membrane

An antibody-immobilized membrane was prepared by immobilizing an antibody onto a nitrocellulose membrane (HiFlow Plus HF240 with a plastic lining, Millipore) cut in the size of 25 mm×200 mm, in the following manner. The membrane was oriented with one of its long sides facing downwards, and was coated, at a position of 8 mm from the bottom, with a solution of anti-myoglobin monoclonal antibody for immobilization (Anti-h Myoglobin 7004 SP-1, Medix Biochemica) prepared at a concentration of 0.5 mg/mL, in a line shape having a width of about 1 mm, with use of an inkjet type applicator (BioDot). In a similar manner, the membrane was also coated, at a position of 12 mm from the bottom, with a solution of anti-cardiac troponin I monoclonal antibody (Anti-hcTNI 9705 SPRN-5, Medix Biochemica) prepared at a concentration of 0.5 mg/mL, in a line-shape. The coated membrane was dried at 50° C. for 30 minutes with a hot-air dryer. The membrane was immersed in 500 ml of a blocking solution (50 mM borate buffer (pH 8.5) containing 0.5 weight % casein (milk-derived, Product No. 030-01505, Wako Pure Chemical Industries)) in a vat, which was then left standing for 30 minutes. Thereafter, the membrane was transferred and immersed into 500 mL of a washing/stabilizing solution (50 mM Tris-HCl (pH 7.5) containing 0.5 weight % sucrose and 0.05 weight % sodium cholate) in a similar vat, which was then left standing for 30 minutes. The membrane was taken out from the solution, and dried at room temperature overnight to yield an antibody-immobilized membrane.

Example 12

Preparation of Immunochromatographic Membrane and Kit

The antibody-immobilized membrane prepared in Example 11 was adhered to a back pressure-sensitive adhesive sheet 1 (ARcare 9020, NIPPN TechnoCluster). At this time, the membrane was oriented so that the long side with the line of anti-myoglobin antibody, among two long sides of the membrane, faced downwards. The bottom side of the antibody-immobilized membrane was adhered with a reaction solution holding pad to be overlapped by about 2 mm. Then, the bottom side of the reaction solution holding pad was adhered with a sample addition pad (glass fiber pad (Glass Fiber Conjugate Pad, Millipore) cut in the size of 18 mm×150 mm to be overlapped by about 4 mm. Further, the top side of the antibody-immobilized membrane was adhered with a lamination of four sheets of absorbent pads (cellulose membranes cut in the size of 20 mm×150 mm each (Cellulose Fiber Sample Pad, Millipore)) to be overlapped by about 5 mm. Thus adhered member was cut with a guillotine cutter (CM4000, NIPPN TechnoCluster) in parallel to the short side of the member so that the long side of the member was cut at 5 mm intervals, to thereby prepare immunochromatographic strips of 5 mm×55 mm. These strips were placed in a plastic case (NIPPN TechnoCluster) for use as a testing immunochromatographic kit.

Example 13

Simultaneous Assay of Myoglobin and Cardiac Troponin I

A mixed solution of anti-cardiac troponin I antibody-labeled fluorescent particles (diameter of 500 nm) and anti-myoglobin antibody-labeled fluorescent particles (diameter of 100 nm) at respective solid concentrations of 0.01% in 1% BSA-containing PBS (pH 7.4) was prepared, and it is referred to as a reaction solution C.

Solutions (1) to (5) containing myoglobin and cardiac troponin I at concentrations shown in Table 2 in 1% BSA-containing PBS (pH 7.4) were prepared, and are referred to as reaction solution D.

The reaction solution C (50 μL) and the reaction solution D (50 μL) were mixed and left still for 1 minute, the total amount of which was then dropped on the immunochromatographic kit produced in Example 12, followed by development of the solution. 15 minutes after the development, the fluorescence intensities of myoglobin and cardiac troponin I on the test line were measured with an image analyzer (LAS-4000, FUJIFILM). The relationships between the concentrations and the fluorescence intensities of myoglobin and cardiac troponin I are shown in Table 2.

TABLE 2

|  | (1) | (2) | (3) | (4) | (5) |
|---|---|---|---|---|---|
| Cardiac troponin I | 1.0E−12 ⊚ | 1.0E−11 ⊚ | 1.0E−10 ⊚ | 1.0E−09 ◯ | 1.0E−08 ◯ |
| Myoglobin | 1.0E−12 X | 1.0E−11 X | 1.0E−10 ⊚ | 1.0E−09 ⊚ | 1.0E−08 ⊚ |

⊚: Quantifiable
◯: Detectable
X: Undetectable

Example 14

Production of Fluorescent Particles (Diameter of 500 nm) Labeled With Anti-myoglobin Antibodies In 250 μL of 2% fluorescent particle solution (F8812, diameter of 500 nm, Molecular Probes) were added 150 μL of 50 mM MES buffer (pH 6.0) and 100 μL of 5.0 mg/mL anti-myoglobin monoclonal antibody solution (Anti-hMyoglobin 7001 SPR-1, Medix Biochemica), followed by stirring at room temperature for 15 minutes. 5 μL of 400 mg/mL WSC aqueous solution (Product No. 01-62-0011, Wako Pure Chemical Industries) was added thereto, followed by stirring at room temperature overnight. 50 μL of 2 mol/L glycine aqueous solution was added thereto, followed by stirring for 30 minutes. The mixture was then centrifuged (at 15,000 rpm at 4° C. for 30 minutes) to effect precipitation of particles. The supernatant was removed. The remaining matter was added with 500 μL of PBS (pH 7.4), followed by re-dispersion of the fluorescent particles with an ultrasonic washer. The mixture was further centrifuged (at 15,000 rpm at 4° C. for 30 minutes), and the supernatant was removed. Then, the remaining matter was added with 500 μL of 1% BSA-containing PBS solution (pH 7.4), followed by re-dispersion of the fluorescent particles to thereby yield an antibody-labeled fluorescent particle solution.

Example 15

Production of Fluorescent Particles (Diameter of 100 nm) Labeled With Anti-cardiac Troponin I Antibodies In 250 μL of 2% fluorescent particle solution (F8801, diameter of 100 nm, Molecular Probes) were added 150 μL of 50 mM MES buffer (pH 6.0) and 100 μL of 5.0 mg/mL anti-cardiac troponin I monoclonal antibody solution (Anti-hcTNI 9701 SPRN-5, Medix Biochemica), followed by stirring at room temperature for 15 minutes. 5 μL of 400 mg/mL WSC aqueous solution (Product No. 01-62-0011, Wako Pure Chemical Industries) was added thereto, followed by stirring at room temperature overnight. 50 μL of 2 mol/L glycine aqueous solution was added thereto, followed by stirring for 30 minutes. The mixture was then centrifuged (at 15,000 rpm at 4° C. for 30 minutes) to effect precipitation of particles. The supernatant was removed. The remaining matter was added with 500 μL of PBS (pH 7.4), followed by re-dispersion of the fluorescent particles with an ultrasonic washer. The mixture was further centrifuged (at 15,000 rpm at 4° C. for 30 minutes), and the supernatant was removed. Then, the remaining matter was added with 500 μL of 1% BSA-containing PBS solution (pH 7.4), followed by re-dispersion of the fluorescent particles to thereby yield an antibody-labeled fluorescent particle solution.

Comparative Example 1

Simultaneous Assay of Myoglobin and Cardiac Troponin I

A mixed solution of anti-cardiac troponin I antibody-labeled fluorescent particles (diameter of 500 nm) and anti-myoglobin antibody-labeled fluorescent particles (diameter of 500 nm) at respective solid concentrations of 0.01% in 1% BSA-containing PBS (pH 7.4) was prepared, and it is referred to as a reaction solution C.

Solutions (1) to (5) containing myoglobin and cardiac troponin I at concentrations shown in Table 3 in 1% BSA-containing PBS (pH 7.4) were prepared, and are referred to as a reaction solution D.

The reaction solution C (50 μL) and the reaction solution D (50 μL) were mixed and left still for 1 minute, the total amount of which was then dropped on the immunochromatographic kit produced in Example 12, followed by development of the solution. 15 minutes after the development, the fluorescence intensities of myoglobin and cardiac troponin I on the test line were measured with an image analyzer (LAS-4000, FUJIFILM). The relationships between the concentrations and the fluorescence intensities of myoglobin and cardiac troponin I are shown in Table 3.

TABLE 3

|  | (1) | (2) | (3) | (4) | (5) |
| --- | --- | --- | --- | --- | --- |
| Cardiac troponin I | 1.0E−12 ⊚ | 1.0E−11 ⊚ | 1.0E−10 ⊚ | 1.0E−09 ○ | 1.0E−08 ○ |
| Myoglobin | 1.0E−12 ○ | 1.0E−11 ○ | 1.0E−10 ○ | 1.0E−09 ○ | 1.0E−08 ○ |

⊚: Quantifiable
○: Detectable
X: Undetectable

Comparative Example 2

Simultaneous Assay of Myoglobin and Cardiac Troponin I

A mixed solution of anti-cardiac troponin I antibody-labeled fluorescent particles (diameter of 100 nm) and anti-myoglobin antibody-labeled fluorescent particles (diameter of 100 nm) at respective solid concentrations of 0.01% in 1% BSA-containing PBS (pH 7.4) was prepared, and it is referred to as a reaction solution C.

Solutions (1) to (5) containing myoglobin and cardiac troponin I at concentrations shown in Table 4 in 1% BSA-containing PBS (pH 7.4) were prepared, and referred to as a reaction solution D.

The reaction solution C (50 μL) and the reaction solution D (50 μL) were mixed and left still for 1 minute, the total amount of which was then dropped on the immunochromatographic kit produced in Example 12, followed by development of the solution. 15 minutes after the development, the fluorescence intensities of myoglobin and cardiac troponin I on the test line were measured with an image analyzer (LAS-4000, FUJIFILM). The relationships between the concentrations and the fluorescence intensities of myoglobin and cardiac troponin I are shown in Table 4.

TABLE 4

|  | (1) | (2) | (3) | (4) | (5) |
| --- | --- | --- | --- | --- | --- |
| Cardiac troponin I | 1.0E−12 X | 1.0E−11 X | 1.0E−10 X | 1.0E−09 ○ | 1.0E−08 ○ |
| Myoglobin | 1.0E−12 X | 1.0E−11 X | 1.0E−10 ⊚ | 1.0E−09 ⊚ | 1.0E−08 ⊚ |

⊚: Quantifiable
○: Detectable
X: Undetectable

The invention claimed is:

1. An immunoassay method which comprises:
    (a) applying simultaneously or sequentially onto a chromatographic insoluble carrier a plurality of different test substances and first binding substances each labeled with particulate labels having different preselected particle sizes but having a same optical characteristic, wherein the first binding substances each specifically bind to the corresponding test substances;
    (b) capturing complexes of the test substances and the first binding substances labeled with particulate labels by second binding substances each specific for the corresponding test substances in different reaction portions of the chromatographic insoluble carrier, wherein each of the second binding substances is immobilized in each of the different reaction portions; and
    (c) measuring the same optical characteristic of the particulate labels, so as to simultaneously detect the plurality of different test substances,
    wherein the plurality of different test substances have different detectable concentration ranges.

2. The immunoassay method according to claim 1, wherein the plurality of different test substances and the first binding substances labeled with particulate labels are applied onto the chromatographic insoluble carrier, in a state where complexes thereof are being formed.

3. The immunoassay method according to claim 1, wherein a sample containing the plurality of different test substances is applied onto the chromatographic insoluble carrier, and further then the first binding substances labeled with particulate labels are applied onto the chromatographic insoluble carrier.

4. The immunoassay method according to claim 1, wherein said optical characteristic is absorbance, scattered light intensity, or fluorescence intensity.

5. The immunoassay method according to claim 1, wherein said particulate labels are fluorescent particles, colored particles, or noble metal particles.

6. The immunoassay method according to claim 1, wherein the first and second binding substances are antibodies.

7. The immunoassay method according to claim 1, wherein in step (c) the same optical characteristic of the particulate labels is measured under a same analysis condition.

* * * * *